United States Patent
Binner et al.

(10) Patent No.: US 10,821,297 B2
(45) Date of Patent: Nov. 3, 2020

(54) KIT AND METHOD FOR TOPICAL DELIVERY OF BENEFITS

(71) Applicant: Johnson & Johnson Consumer Inc., Skillman, NJ (US)

(72) Inventors: Curt Binner, Furlong, PA (US); Alexandru Paunescu, Clinton, NJ (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 601 days.

(21) Appl. No.: 15/705,776

(22) Filed: Sep. 15, 2017

(65) Prior Publication Data
US 2018/0093106 A1 Apr. 5, 2018

Related U.S. Application Data

(60) Provisional application No. 62/402,216, filed on Sep. 30, 2016.

(51) Int. Cl.
*A61N 5/06* (2006.01)
*A61K 8/34* (2006.01)
(Continued)

(52) U.S. Cl.
CPC ............ *A61N 5/0616* (2013.01); *A61F 7/007* (2013.01); *A61F 7/02* (2013.01); *A61K 8/0208* (2013.01);
(Continued)

(58) Field of Classification Search
CPC .................. A61N 5/0616; A61N 5/062; A61N 2005/0645; A61M 2037/0007; A61F 7/02; A61F 7/007
See application file for complete search history.

(56) References Cited

U.S. PATENT DOCUMENTS 6,162,211 A 12/2000 Tankovich et al.
6,251,100 B1 6/2001 Flock et al.
(Continued)

FOREIGN PATENT DOCUMENTS

WO WO 1999/051296 A1 10/1999
WO WO 2009/066294 A1 5/2009

OTHER PUBLICATIONS

International Search Report dated Dec. 11, 2017, Application No. PCT/US2017/052407.

*Primary Examiner* — Laura A Bouchelle

(57) ABSTRACT

A system for delivering energy to an isolated part of a mammalian body includes an electrically powered patch and a self-supporting adhesive film. The patch has a major surface and comprises a matrix of at least one flexible, biocompatible material which is capable of conforming to the isolated body part. The self-supporting adhesive film has a first non-tacky surface arranged and configured for releasable attachment to the patch and a second tacky surface, opposite the first surface, for adhesive attachment to the isolated body part. The releasable attachment between the self-supporting adhesive film and the electrically powered patch has a lower strength than the adhesive attachment between the film and the isolated body part. Thus, during use the electrically powered patch is removable from the self-supporting adhesive film while leaving the self-supporting adhesive film adhered to the isolated body part.

17 Claims, 4 Drawing Sheets

(51) Int. Cl.

| | | |
|---|---|---|
| A61K 47/32 | (2006.01) | |
| A61K 47/46 | (2006.01) | |
| A61K 31/60 | (2006.01) | |
| A61K 47/38 | (2006.01) | |
| A61Q 19/08 | (2006.01) | |
| A61F 7/02 | (2006.01) | |
| A61N 1/32 | (2006.01) | |
| A61N 1/40 | (2006.01) | |
| A61F 7/00 | (2006.01) | |
| A61N 1/04 | (2006.01) | |
| A61N 7/02 | (2006.01) | |
| A61K 8/81 | (2006.01) | |
| A61K 8/02 | (2006.01) | |
| A61K 9/00 | (2006.01) | |

(52) U.S. Cl.
CPC .............. *A61K 8/345* (2013.01); *A61K 8/347* (2013.01); *A61K 8/8176* (2013.01); *A61K 9/0002* (2013.01); *A61K 9/0009* (2013.01); *A61K 31/60* (2013.01); *A61K 47/32* (2013.01); *A61K 47/38* (2013.01); *A61K 47/46* (2013.01); *A61N 1/0404* (2013.01); *A61N 1/0472* (2013.01); *A61N 1/0492* (2013.01); *A61N 1/325* (2013.01); *A61N 1/328* (2013.01); *A61N 1/40* (2013.01); *A61N 7/02* (2013.01); *A61Q 19/08* (2013.01); *A61F 2007/0052* (2013.01); *A61F 2007/0071* (2013.01); *A61F 2007/0075* (2013.01); *A61F 2007/0078* (2013.01); *A61F 2007/0093* (2013.01); *A61F 2007/0226* (2013.01); *A61K 2800/805* (2013.01); *A61K 2800/83* (2013.01); *A61K 2800/87* (2013.01); *A61K 2800/88* (2013.01); *A61N 2005/0643* (2013.01); *A61N 2005/0651* (2013.01); *A61N 2005/0652* (2013.01); *A61N 2005/0665* (2013.01)

(56) References Cited

U.S. PATENT DOCUMENTS

| | | |
|---|---|---|
| 7,070,611 B2 | 7/2006 | Biel |
| 8,478,396 B2 | 7/2013 | Tsao |
| 8,801,254 B2 | 8/2014 | McNeill |
| 8,840,929 B2 | 9/2014 | Bickford |
| 8,852,616 B2 | 10/2014 | Bickford |
| 8,862,223 B2 | 10/2014 | Yanaki |
| 8,877,508 B2 | 11/2014 | Hyde |
| 8,894,635 B2 | 11/2014 | Behrakis |
| 9,067,062 B2 | 6/2015 | Hilty |
| 2001/0050083 A1 | 12/2001 | Marchitto |
| 2005/0038473 A1 | 2/2005 | Tamarkin et al. |
| 2006/0024358 A1 | 2/2006 | Santini et al. |
| 2007/0036847 A1* | 2/2007 | Yoshinaga ........... A61K 9/7053 424/448 |
| 2007/0208395 A1* | 9/2007 | Leclerc ................ A61N 5/0616 607/86 |
| 2007/0233208 A1 | 10/2007 | Kurtz et al. |
| 2008/0188791 A1 | 8/2008 | Difiore |
| 2009/0198173 A1 | 8/2009 | Samuel et al. |
| 2010/0179469 A1 | 7/2010 | Hammond |
| 2012/0289885 A1* | 11/2012 | Cottrell ................ A61N 5/0616 604/20 |
| 2013/0116616 A1 | 5/2013 | Buchholz |
| 2013/0190845 A1 | 7/2013 | Liu et al. |
| 2014/0135874 A1 | 5/2014 | Dean |
| 2015/0182990 A1 | 7/2015 | Binner et al. |
| 2015/0182991 A1 | 7/2015 | Binner et al. |
| 2015/0182992 A1 | 7/2015 | Binner et al. |
| 2015/0182993 A1 | 7/2015 | Binner et al. |
| 2015/0290028 A1 | 10/2015 | Isserow |
| 2016/0015962 A1 | 1/2016 | Shokoueinejad Maragheh et al. |

* cited by examiner

KIT AND METHOD FOR TOPICAL DELIVERY OF BENEFITS

CROSS-REFERENCE TO RELATED APPLICATIONS

This application claims the benefit of U.S. provisional application 62/402,216 filed on Sep. 30, 2016.

FIELD OF THE INVENTION

The present invention relates to a system for providing benefits to an isolated part of a mammalian body. More specifically, the present invention is directed to a method of topical application of energy and optionally benefit agent(s) to address common consumer skin flaws with a system including an electrically powered patch used in combination with a self-supporting adhesive film for topical delivery of benefits to the consumer, and kits comprising the patch and self-supporting adhesive film.

BACKGROUND OF THE INVENTION

Mankind's quest for ageless, flawless, youthful skin appearance is ceaseless. Common skin flaws include: acne, age spots, birthmarks, dry skin, eczema, hyperpigmentation, large pores, moles, psoriasis, rosacea, scars, sun spots, under eye circles, warts, and wrinkles.

Consumers are always looking for the next product or treatment that will treat these flaws and keep them younger looking, and in particular, safer and more effective methods and products for rejuvenating the skin. There are many known formulation in the form of creams, lotions, powders and oils which consumers apply to their face, hands, feet and bodies specifically targeting the various common skin flaws. Many have active substances for use in treating the flaws.

Combinations of cosmetic formulations and electrically powered stimulations have been found to be useful in the treatment of cosmetic flaws. Formulations may be applied to the consumer's skin, and then the treatment area is exposed to light, heat, cooling, or vibration.

The formulations may be washed off immediately, or left on for longer periods, such as overnight, to allow longer term contact between the skin and the active containing formulation.

Skin treatment patches containing electrically powered components for use with, or containing, active substances have been reported. A skin treating formulation can be applied to the consumer's skin at the treatment sight, with the electrically powered patch disposed on the formulation. When the treatment time is completed, the electrically powered patch is removed from the formulation.

As mentioned earlier, there is often a desire to leave the active containing formulations on the skin for longer periods, such as overnight, to allow longer term contact between the skin and the active containing formulation. A disadvantage of the above combination use of electrically powered patches with skin treating formulations is that once the electrically powered patch is removed from the skin, the formulation is exposed to the environment. In cases where the formulation is in the form of creams, lotions, powders or oils, the formulation could be rubbed off unintentionally by the consumer, such as onto the surface of pillows or sheets if the consumer would like to leave the formulation overnight while sleeping. This results in less active substance on the site of treatment, as well as unwanted stains on the consumer's bed linens.

The rubbing off or staining is often due to the stickiness of the components of the creams, lotions, powders or oils. This may be prevented by leaving the electrically powered patch on overnight to cover the active containing formulation. However, electrically powered patches can be bulky and therefore uncomfortable to leave on the consumer, especially on the face, and especially overnight.

In summary, coupling electrically powered patches with a self-supporting adhesive film to deliver a benefit to address common skin flaws. Often, there is a desire for the consumer to leave an active formulation on overnight for longer treatment. This can result in the formulation rubbing off of the skin and onto the consumer's bed linen. Known formulations/electrically powered stimulating patch combinations are limited in their abilities to avoid these issues. What is needed are methods, devices, and kits to avoid these limitations.

SUMMARY OF THE INVENTION

Surprisingly, we have found that a system for delivering energy to an isolated part of a mammalian body including an electrically powered patch and a self-supporting adhesive film can overcome the failures in the prior art. In particular, the electrically powered patch has a major surface and comprising a matrix of at least one flexible, biocompatible material which is capable of conforming to the isolated body part and having associated therewith at least one active element electrically connected to a controller and a power source. The self-supporting adhesive film has a first non-tacky surface arranged and configured for releasable attachment to the major surface of the electrically powered patch and a second tacky surface, opposite the first surface, for adhesive attachment to the isolated body part. The releasable attachment between the self-supporting adhesive film to the major surface of the electrically powered patch has a lower strength than the adhesive attachment between the self-supporting adhesive film to the isolated body part. Thus, during use the electrically powered patch is removable from the self-supporting adhesive film while leaving the self-supporting adhesive film adhered to the isolated body part.

In another embodiment, a kit for delivering energy to an isolated part of a mammalian body includes an electrically powered patch and a supply of self-supporting adhesive films. The electrically powered patch has a major surface and comprising a matrix of at least one flexible, biocompatible material which is capable of conforming to the isolated body part and having associated therewith at least one active element electrically connected to a controller and a power source. Each of such self-supporting adhesive films has a first non-tacky surface arranged and configured for releasable attachment to the major surface of the electrically powered patch and a second tacky surface, opposite the first surface, for adhesive attachment to the isolated body part. The self-supporting adhesive film may further include one or more benefit agents to be delivered to the isolated body part. The releasable attachment between the self-supporting adhesive film to the major surface of the electrically powered patch has a lower strength than the adhesive attachment between the self-supporting adhesive film to the isolated body part. Thus, during use the electrically powered patch is removable from the self-supporting adhesive film while leaving the self-supporting adhesive film adhered to the isolated body part.

In other aspects, the invention relates to methods of using the system.

DETAILED DESCRIPTION OF THE INVENTION

The present invention relates to systems for delivering active substances to an isolated part of a mammalian body and methods employing the system. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

As used herein the specification and the claims, the term "Topical" and variants thereof mean "of or applied to an isolated part of the body". This includes, without limitation skin, mucosa, and enamel.

Figure 1:
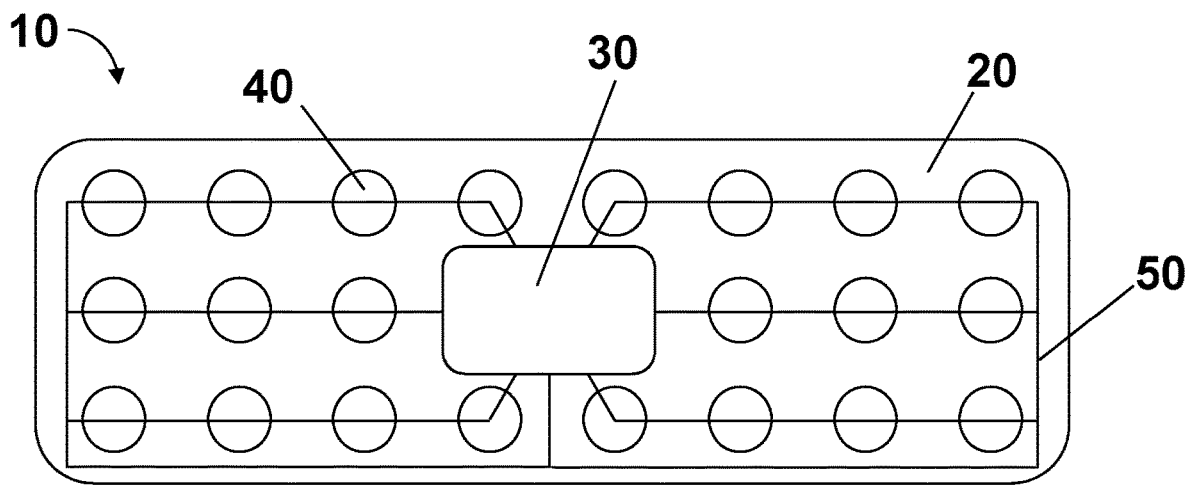
FIG. 1 is a top schematic view of a first embodiment of an electrically powered patch portion of the present invention.
Figure 2:
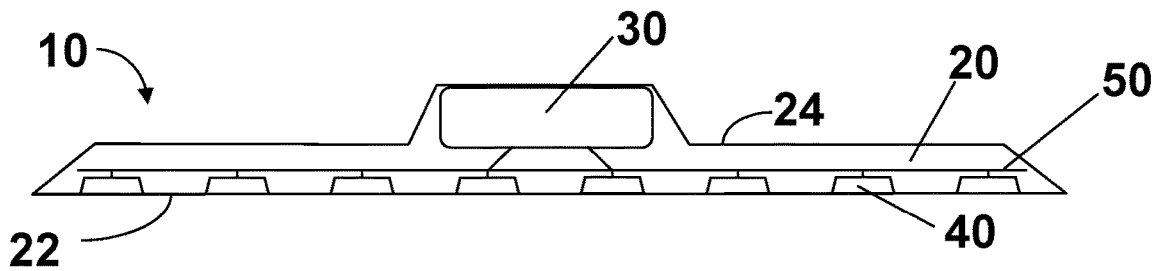
FIG. 2 is a side schematic view of the electrically powered patch embodiment of FIG. 1.

The method for treating common consumer skin flaws described herein uses an electrically powered patch in combination with at least one self-supporting adhesive film for topical delivery benefits to a consumer, and kits comprising the patch and film structure. Electrically powered patch has a major surface and is made of at least one flexible, biocompatible material which is capable of conforming to the isolated body part and having associated therewith at least one active element electrically connected to a controller and a power source, such as a battery, preferably a rechargeable battery. Film structure is a self-supporting adhesive film having a first surface arranged and configured for releasable attachment to the major surface of the electrically powered patch and a second surface, opposite the first surface, for adhesive attachment to the isolated body part Referring to the drawings, FIGS. 1 and 2 are top and side views, respectively, of a first embodiment of an electrically powered patch 10 which may be used in the present invention. The electrically powered patch 10 includes a matrix 20 having a first surface 22, and a second surface 24. Electrically powered patch 10 also has a controller, such as a control panel 30 with an associated power source, such as a battery, and active elements 40. Control panel 30 and active elements 40 are interconnected by conductor 50. While the power source is shown associated with the control panel 30, electrically powered patch 10 also has a controller, such as a control panel 30, it may also be separately disposed on the electrically powered patch 10.

Matrix 20 is made of a flexible, biocompatible material which is capable of forming to the site of treatment on the skin of the consumer. In some embodiments, matrix 20 fully incorporates control panel 30, active elements 40 and conductor 50 elements. This would allow for complete isolation of the elements from ambient humidity, moisture, sweat which may occur during use of patch 10. In other embodiments, active elements 40 may be exposed on first or second surface (22, 24) of matrix 20. The first surface 22 is a major surface to which a self-supporting adhesive film 100 (described below) can be attached.

There are numerous flexible, biocompatible material materials which may be used to form matrix 20. These materials include, but are not limited to silicones, polyurethanes, and polyethylenes. In some embodiments, matrix 20 comprises a low durometer silicone, e.g., durometers in the range of about Shore 10A- to about Shore 30A.

In other embodiments, matrix 20 may be a composite of flexible and more rigid components. Materials of construction include polymers and elastomers, including without limitation, thermoplastic elastomers ("TPE"), thermoplastic urethanes ("TPU"), silicones, acrylonitrile butadiene styrene polymers ("ABS"), among may flexible and more rigid materials. Preferably, the materials include sufficient transmissive properties to transmit the energy, e.g., light, electromagnetic field, microcurrent, electrical stimulation (TENS trans-cutaneous electrical nerve stimulation, MENS, PENS), iontophoresis, sonophoresis, and/or motion, e.g., ultrasound and/or vibration to the treatment surface.

Matrix 20 may have various sizes and shapes depending on the location of use for the patch/film structure device. Possible shapes of the footprint left by matrix 20 include, but are not limited to, squares, rectangles, triangles, circles, ovals, kidneys, stars, crosses, characters, etc. The corners of such shapes, if any, may be angular or curved to reduce potential lift/removal points. The area of the treatment could be greater than about 1,000 cm$^2$, about 1,000 cm$^2$, or about 100 cm$^2$, or about 10 cm$^2$, or about 1 cm$^2$, or less than 1 cm$^2$.

Matrix 20 may have additional structural elements to enhance the delivery of energy through first surface 22. For example, a light-based system may benefit from a reflective enhancement, such as a reflective coating at second surface 24 to redirect light back toward the first surface 22. This may be treated to improve light scattering to provide a more uniform delivery of light through the first surface 22. In certain embodiments in which heat transfer is relevant to the performance of the system, heat-transfer components (for absorbing, guiding, and/or dissipating heat) and/or particles may be disposed within or at the first surface 22 of the matrix 20 or in a coupling film, described below.

Alternatively, the matrix itself may be opaque to prevent light emitted through first surface 22 from returning into matrix 20. Alternatively, a thermal system may benefit from insulating layer at second surface 24 and/or an insulating filler within matrix 20.

For delivery of motion, such as vibration, portions of the matrix may be stiffened and/or tuned to the motion frequency for optimum energy transfer through first surface 22.

In some embodiments, control panel 30 is a PCBA (Printed Circuit Board Assembly). A PCBA is the assembly obtained after all printing solder paste on a board and then mounting various components like resistors, ICs (Integrated Circuits), capacitors, transformers, switches, batteries, and other components, and finally solidifying the solder paste and components in situ. In embodiments where matrix 20 fully incorporates control panel 30, the batteries in control panel 30 may be charged through inductive coupling.

Active elements 40 are used in combination with cosmetic formulations when electrically powered stimulation is useful in enhancing the effect of the active substance in the treatment of cosmetic flaws. Stimulation can come from a light source, a heat source, a cooling source, an electricity source, a radiofrequency source, an ultrasound source, or a motion source (vibration).

In some embodiments, the performance of the active substance is enhanced by light. In these embodiments, active elements 40 can be elements that emit light in the form of visible, ultra-violet (UV), or Infra-Red (IR) light. In some embodiments, active elements 40 are light-emitting diodes (LEDs).

In other embodiments, the performance of the active substance is enhanced by heat. In these embodiments, active elements 40 can be elements that produce resistive or inductive heat. In some embodiments, active elements 40 are resistors.

In still other embodiments, the performance of the active substance is enhanced by cooling. In these embodiments, active elements 40 can be elements that produce thermoelectric cooling using the Pelletier effect. In some embodiments, active elements 40 are Pelletier coolers.

In still other embodiments, the performance of the active substance is enhanced by vibration. In these embodiments, active elements 40 can be elements that vibrate or produce vibrations. These include small motors or piezoelectric devices. In some embodiments, active elements 40 are piezoelectric vibrators.

In still other embodiments, the performance of the active substance is enhanced by electricity to provide iontophoresis or electric stimulation. In these embodiments, active elements 40 can be elements that deliver electric current to the skin. These include at least two electrodes per design. In some embodiments, active elements 40 are electrodes. In some embodiments, the electrodes are affixed to a single adhesive film layer. In other embodiments, each electrode may be affixed to the skin with multiple unique adhesive layers.

In still other embodiments, the performance of the active substance is enhanced by radiofrequency. In these embodiments, active elements 40 can be elements that generate radiofrequency signals. These include radio generators and transmitters. In some embodiments, active elements 40 are electronic oscillators.

In still other embodiments, the performance of the active substance is enhanced by ultrasound. In these embodiments, active elements 40 can be elements that produce ultrasonic energy. These include ultrasonic horns or speakers. In some embodiments, active elements 40 are ultrasonic generators.

Although FIG. 1 shows approximately twenty active elements 40, the number of active elements 40 in electrically powered patch 10 will depend on the treatment type, intensity, and area being treated. The number of active elements 40 in electrically powered patch 10 could be 1, or 2, or 5, or 10, or 20 or 100 or more.

Possible cross-sectional shapes of active elements 40 include, but are not limited to, squares, rectangles, triangles, circles, ovals, kidneys, stars, crosses, characters, etc. The corners of such shapes, if any, may be angular or curved to reduce potential lift/removal points.

Conductor 50 connects control panel 30 to active elements 40, and may be in the form of wires or filaments. They may be made of metallic or nonmetallic conducting materials. Metallic conducting materials include copper, aluminum and silver. Nonmetallic conducting materials include carbon, such as graphite, or conductive polymers.

Although FIG. 1 shows a regular array of active elements 40, the arrangement of these elements need not be a regular array. For example, one may desire to concentrate active elements in certain portions of the patch, and reduce the frequency/density of active elements in other portions of the patch. In addition, active elements may be placed around the periphery of the electrically powered patch and be coupled a wave guide that evenly distributes the energy, such as light energy, throughout the patch for delivery to the first surface for delivery to the user's skin. In other embodiments, the patch 10 may be shaped for application in alternative orientations, such as rotating an elongate patch 180° from one use to another, and the active elements 40 may be arranged about the patch 10 such that such rotation places the active elements 40 in a different location within the treatment area.

Figure 3:
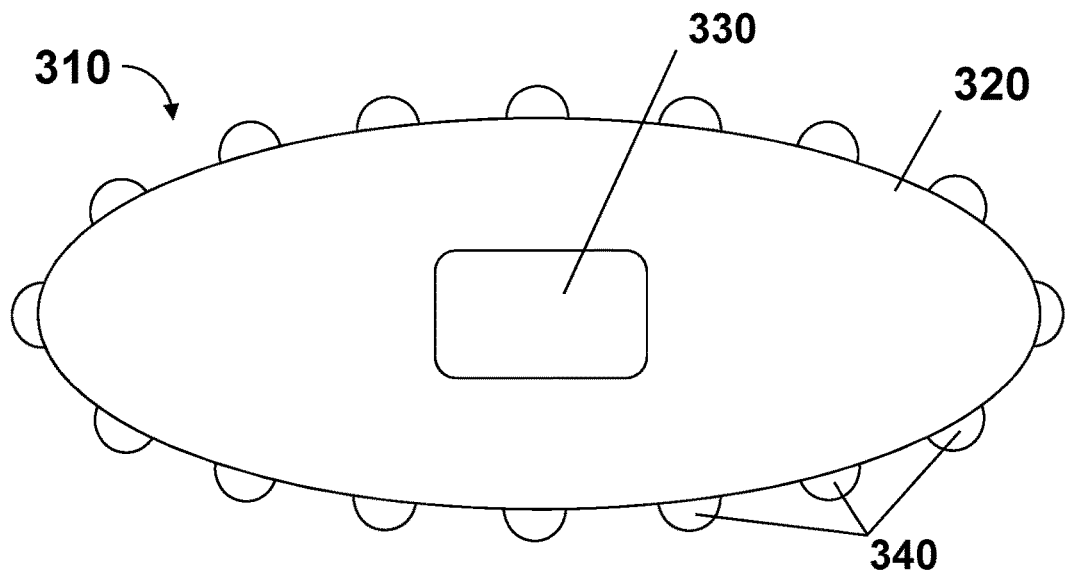
FIG. 3 is a top schematic view of a second embodiment of an electrically powered patch portion of the present invention.
Figure 4:
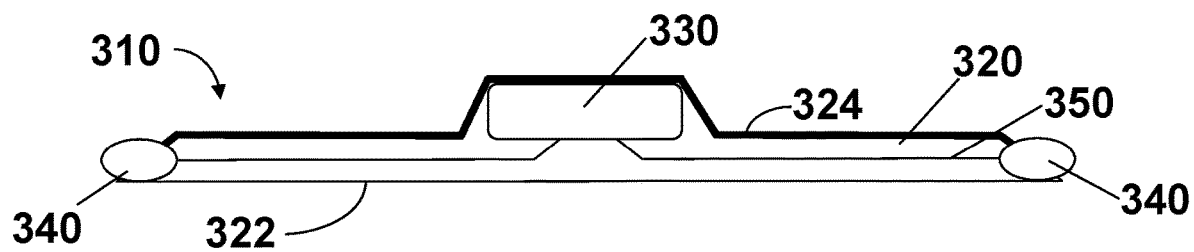
FIG. 4 is a side schematic view of the electrically powered patch embodiment of FIG. 3.

FIGS. 3 and 4 are top and side views, respectively, of a second embodiment of an electrically powered patch 310 which may be used in the present invention. The electrically powered patch 310 includes a matrix 320 having a first surface 322, and a second surface 324. Electrically powered patch 310 also has a controller, such as a control panel 330 and active elements 340. Control panel 330 and active elements 340 are interconnected by conductor 350.

Matrix 320 is made of a flexible, biocompatible material which is capable of forming to the site of treatment on the skin of the consumer. In some embodiments, matrix 320 fully incorporates control panel 330, active elements 340 and conductor 350 elements. This would allow for complete isolation of the elements from ambient humidity, moisture, sweat which may occur during use of patch 310. In other embodiments, active elements 340 may be exposed on first or second surface (322, 324) of matrix 320. The first surface 322 is a major surface to which a self-supporting adhesive film 100 (described below) can be attached.

As mentioned above, there are numerous flexible, biocompatible material materials which may be used to form matrix 320, low durometer silicone, e.g., durometers in the range of about Shore 10A- to about Shore 30A.

Matrix 320 may have various sizes and shapes depending on the location of use for the patch/film structure device. Possible shapes of the footprint left by matrix 320 include, but are not limited to, squares, rectangles, triangles, circles, ovals, kidneys, stars, crosses, characters, etc. The corners of such shapes, if any, may be angular or curved to reduce potential lift/removal points. The area of the treatment could be greater than about 1,000 $cm^2$, about 1,000 $cm^2$, or about 100 $cm^2$, or about 10 $cm^2$, or about 1 $cm^2$, or less than 1 $cm^2$.

In this embodiment, matrix 320 has an additional structural element to enhance the delivery of energy through first surface 323. Here, second surface 324 has a reflective coating to redirect energy back toward first surface 322. In the case of active elements 340 being light sources, this may improve light scattering to provide a more uniform delivery of light through first surface 322.

In certain embodiments, such as shown in FIG. 3, Matrix 320 may provide desirable optical properties (including shielding, reflecting, and/or refracting) to act as a light guide. In such embodiments, the light sources 340 may be disposed about the periphery of the matrix 320. Such an embodiment may also incorporate light-extracting elements, such as diffractive optics, light conversion (e.g., wavelength shift), etc.

Alternatively, or in addition, matrix 320 may be opaque to prevent light emitted through first surface 322 from returning into matrix 320. Alternatively, a thermal system may benefit from insulating layer at second surface 324 and/or an insulating filler within matrix 320.

For delivery of motion, such as vibration, portions of matrix 320 may be stiffened and/or tuned to the motion frequency for optimum energy transfer through first surface 322.

Similar to first embodiment, control panel 330 may be a PCBA (Printed Circuit Board Assembly), with various components like resistors, ICs (Integrated Circuits), capacitors, transformers, switches, batteries, and other components. In embodiments where matrix 320 fully incorporates control panel 330, the batteries in control panel 330 may be charged through inductive coupling.

Active elements 340 are used in combination with cosmetic formulations when electrically powered stimulation is useful in enhancing the effect of the active substance in the treatment of cosmetic flaws. Stimulation can come from a light source, a heat source, a cooling source, or a motion source (vibration).

In some embodiments, the performance of the active substance is enhanced by light, heat, cooling, or vibration.

Although FIG. 3 shows sixteen active elements 340, the number of active elements 340 in electrically powered patch 310 will depend on the treatment type, intensity, and area being treated. The number of active elements 340 in electrically powered patch 310 could be 1, or 2, or 5, or 10, or 20 or 100 or more.

Possible cross-sectional shapes of active elements 340 include, but are not limited to, squares, rectangles, triangles, circles, ovals, kidneys, stars, crosses, characters, etc. The corners of such shapes, if any, may be angular or curved to reduce potential lift/removal points.

Conductor 350 connects control panel 330 to active elements 340, and may be in the form of wires or filaments. They may be made of metallic or nonmetallic conducting materials. Metallic conducting materials include copper, aluminum and silver. Nonmetallic conducting materials include graphite or conductive polymers.

Figure 5:
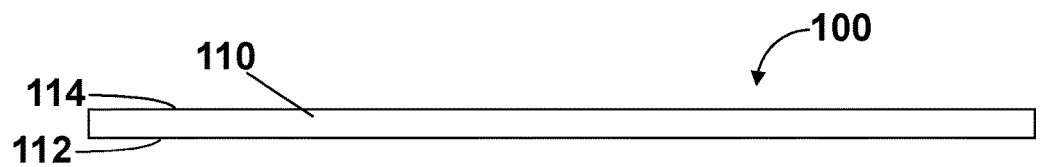
FIG. 5 is a side schematic view of a first embodiment of a self-supporting adhesive film portion of the present invention.
Figure 6:
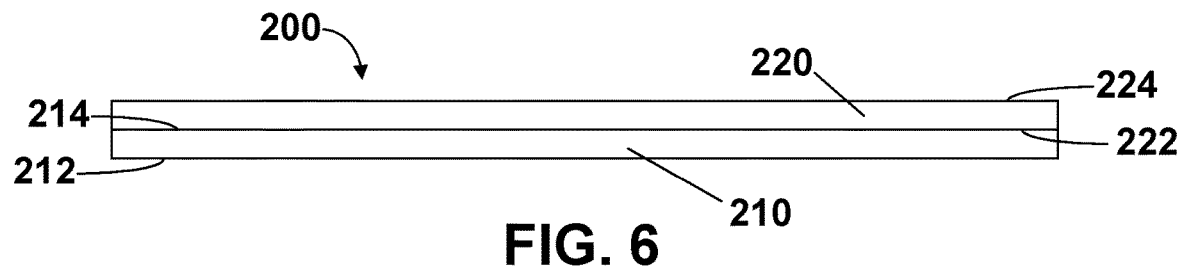
FIG. 6 is a side schematic view of a second embodiment of a self-supporting adhesive film portion of the present invention.

FIGS. 5 and 6 are side views of first and second, respectively, embodiments of a self-supporting adhesive film which may be used in the present invention. First embodiment self-supporting adhesive film 100 of the present invention, illustrated in FIG. 5, includes a matrix 110 having a first skin-contacting surface 112, and a second, non skin-contacting surface 114.

Second embodiment self-supporting adhesive film 200 of the present invention, illustrated in FIG. 6, has bottom, skin-contacting layer 210 and top layer 220. Top layer 220 has top surface 224 facing outwardly from the skin, and bottom surface 222 facing towards the skin. Skin-contacting layer 210 has first, skin-contacting surface 212 that adheres to the skin of the user when applied thereto. Skin-contacting layer 210 has second surface 214 opposite first, skin-contacting surface 212, fixedly attached to bottom surface 222 of top layer 220.

The self-supporting adhesive film of the present invention, as shown above and further described herein below, preferably is easy to apply, comfortable to wear, and readily removable, i.e., dispersible by water through disintegration and/or dissolution.

In accordance with a more particular aspect of the present invention, non skin-contacting surface 114 of first embodiment film structure 100, and top surface 224 of second embodiment self-supporting adhesive film 200, both of which are surfaces facing away from the skin of the consumer to whom the film structure is adhered, are non-tacky so that the topically-applied self-supporting adhesive film stays in place at the application site, does not stick to another film structure and does not gather dust, dirt or other debris from the immediately surrounding area. The skin-contacting surface 112 of first embodiment self-supporting adhesive film 100, and skin-contacting surface 212 of second embodiment self-supporting adhesive film 200, are tacky and adhere to skin.

In accordance with a more particular aspect of the present invention, first surface 22 of first embodiment electrically powered patch 10 releasably attaches to non-skin-contacting surface 114 and top surface 224 of first embodiment self-supporting adhesive film 100 and second embodiment self-supporting adhesive film 200, respectively. The attachment strength of electrically powered patch 10 to self-supporting adhesive films 100 and 200 are less than the adhesive strength of the self-supporting adhesive films 100 and 200 to skin.

This relative strength is provided by modifying the material of the electrically powered patch 10, at least on the first surface 22 (the surface that is directed toward the skin during use). As indicted above, a silicone polymeric structure is desirable for the matrix 20 of the electrically powered patch 10. The attachment strength between the first surface 22 of the matrix 20 and the top surface 114 of the self-supporting adhesive film 100 is affected by the surface texture of the first surface 22 of the matrix 20 and by incorporating one or more tackifiers in the material of the matrix 20. If a relatively smooth top surface 114 of the self-supporting adhesive film 100 is to be used, imparting a texture, such as a plurality of parallel grooves, a bead-blasted texture, and the like, to the first surface 22 can increase the attachment strength therebetween. In addition, adding tackifier to the matrix material can increase the attachment strength between the matrix 20 and the self-supporting adhesive film 100.

For example, in one embodiment, matrix 20 comprises a commercially available silicone, such as that sold under the tradename SORTA-CLEAR 18 (Smooth-On, Inc., Easton, Pa.), a low durometer clear two-part silicone that is mixed at a ratio of 1 part hardener to 10 parts resin. The silicone matrix 20 can be modified by the addition of a tackifier, such as that sold under the tradename SLACKER (Smooth-On, Inc., Easton, Pa.). The addition of the tackifier imparts a pressure sensitive adhesive quality into the silicone matrix 20, improving the attachment strength of the matrix 20 to the self-supporting adhesive film 100. The amount of tackifier added affects the attachment strength between the matrix 20 and the self-supporting adhesive film 100. Generally, increasing the amount of tackifier in the matrix 20 will increase its attachment strength to the self-supporting adhesive film 100.

For example, in a first embodiment, a silicone compound made with 1 part hardener to 10 parts resin to 1.5 parts tackifier (by weight) has an adhesive strength of 48 grams, as measured with a probe tack testing apparatus (Texture Technologies (Hamilton, Mass.) TA-XT analyzer with TA-303 Indexable plate with TA-57R probe with a 7 mm circular sample. In a second embodiment, while a silicone compound made with 1 part hardener to 10 parts resin to 2.5 parts tackifier (by weight) has an adhesive strength of 56 grams when measured with the same apparatus.

The relative attachment strength between the self-supporting adhesive film 100 and silicone matrix 20 can further be manipulated with the final surface finish imparted onto the major surface of the silicone matrix 20. As the surface roughness increases, the contact area between silicone and self-supporting adhesive film increases, increasing the attachment strength. An example of this is a silicone matrix 20 comprising of a compound made from 1 part hardener to 10 parts resin to 1.5 parts tackifier (by weight) with a surface roughness of less than about 32 Ra (arithmetic average of absolute values of height of surface imperfections). This structure has an adhesive strength of about 48 grams. In contrast, a silicone matrix 20 comprising the same ratio of components, but with a surface roughness of 16 Ra that gives an adhesive strength of about 75 grams. If the roughness is too great, the attachment strength is reduced because of the effective reduction of surface area on the contact surfaces. For a silicone matrix 20, at 32 Ra the adhesive strength drops back to 48 grams. In some embodiments, surface roughness of silicone matrix 20 is less than about 1 Ra, or less than 16 Ra, or less than 32 Ra.

In order to ensure that electrically powered patch 10 can be removed and self-supporting adhesive film 100 left in place on the user's skin, the adhesive strength of the self-supporting adhesive film 100 to skin is more than the attachment strength of the patch 10 to self-supporting adhesive film 100. In one embodiment, an adhesive strength of 190 grams between the self-supporting adhesive film 100 and skin (as measured by adhesive tack test method described above, using a microcrystalline wax sold under the tradename MULTIWAX W-445 [Witco Chemical Corporation, New York] to simulate skin) gives reliable performance to leave the self-supporting adhesive film 100 in place while electrically powered patch 10 is removed.

Self-supporting adhesive films 100 and 200 are provided in forms that are comfortable, easy to apply to the application site, remains in place for an extended period of time, e.g., at least half an hour, or at least one hour, or at least about six (6) to eight (8) hours, or at least about twelve (12) hours, or about twenty four (24) hours, if desired. Self-supporting adhesive films 100 and 200 are readily removable upon application of water thereto. By readily removable, it is meant that the film structure may dissolve or disintegrate upon application of water to the film structure, such that it may be removed from the skin without scrubbing, or the like. Self-supporting adhesive films 100 and 200 preferably are a topically-applied skin care film, patch, applique, etc. (hereinafter "film structure" for the sake of convenience, without intent to limit) that preferably is relatively flexible.

Self-supporting adhesive films 100 and 200 of the present invention preferably are relatively thin and flexible, as described in further detail below, so that they preferably readily conforms to the user's skin and are comfortable to wear, both because of the flexibility and conformability, as well as from the thinness. Self-supporting adhesive films 100 and 200 of the present invention intended for extended wear preferably are also formed to be aesthetically elegant without either peeling, wrinkling, cracking, or appearing greasy or tacky, or otherwise unpleasant or unsightly in nature. Self-supporting adhesive films 100 and 200 preferably are formed with sufficient rigidity and integrity to be able to withstand normal use when on the skin. For instance, self-supporting adhesive films 100 and 200 of the invention preferably are formed with sufficient strength to stay intact on the skin when exposed to normal external forces that the skin may experience, e.g., rubbing of clothing, pillow, etc.

If desired, self-supporting adhesive films 100 and 200 of the present invention may be formed to have structural integrity. As used herein, structural integrity is to be understood as the physical capability of the self-supporting adhesive film to maintain a substantially monolithic form or structure and to resist tearing or fracture while being manipulated independent of a substrate, and preferably while being applied to an application site. If an additional supporting substrate is used, the film structure preferably is removable from the substrate as an integral film for use independent of the substrate.

It will be appreciated that structural integrity of self-supporting adhesive films 100 and 200 of the present invention preferably also contributes to the self-supporting adhesive film's ability to remain intact during manipulation and use, and to conform to the contours of the application site to which it is applied, as discussed in further detail below. For instance, it is desirable that the self-supporting adhesive film have sufficient structural integrity so that the self-supporting adhesive film does not readily tear when removed from a substrate, manipulated, worn, or otherwise used. It will be appreciated that selection of one or more film formers that contribute to a product's ability to achieve a pliable, cohesive, and continuous covering on an application site such as skin, is one manner of achieving the desired structural integrity of a self-supporting adhesive film of the present invention. Additionally, or alternatively, selection of one or more plasticizers for producing or promoting plasticity and flexibility and reducing brittleness, is another manner of achieving the desired structural integrity of a self-supporting adhesive film of the present invention.

The structural integrity of self-supporting adhesive films 100 and 200 of the present invention typically may be correlated with the tensile strength and thickness of the film structure. In connection with the present invention, structural integrity typically increases as thickness and yield strength increase. However, such properties must be balanced with their effect on whether the self-supporting adhesive film is comfortable to be worn, as discussed in further detail below. Tensile strength contributes to the structural integrity of self-supporting adhesive films 100 and 200 used in accordance with principles of the present invention for such purposes as handling and/or removing the self-supporting adhesive film from a substrate. Tensile strength affects, inter alia, whether the self-supporting adhesive film resists being fractured when being handled and/or removed from a substrate. For instance, self-supporting adhesive films 100 and 200 of the present invention preferably have an elastic modulus of about 500 psi to about 10,000 psi. An elastic modulus of about 2,500 psi has been found in one embodiment to provide the desired stiffness to be comfortable during use. Typical samples with a ¾ inch (1.905 cm) width and a 0.1 mm thickness have a rupture-strength of about 2 lbf (pound force), although it will be appreciated that a useful range of rupture strengths is from about 0.5 lbf to about 5 lbf. The thickness of the self-supporting adhesive film also affects structural integrity. For instance, the thickness of a self-supporting adhesive film of the present invention may be between about 0.05 mm to about 2 mm, and preferably between about 0.05 mm and 0.3 mm. A thickness of approximately 0.1 mm has been found to provide the desired mechanical properties for handling, applying, and ultimately removing the self-supporting adhesive film, such that the self-supporting adhesive film maintains its structural integrity throughout such use, as well as while being worn on a given application site, as discussed in further detail below.

In accordance with one aspect of the present invention, self-supporting adhesive films 100 and 200 of the present invention are self-adhesive, i.e., the self-supporting adhesive film adheres to a user's skin upon contact with the skin, preferably without additional steps, such as addition of another composition, such as water. The adhesive properties may be imparted by at least one water-soluble carbohydrate, such as saccharides (monosaccharides or disaccharides or oligosaccharides or polysaccharides or mixtures thereof). Saccharides have the chemical formula $Cx(H_2O)y$ with the chemical structure $H(CHOH)nC=O(CHOH)mH$. Examples include starch derived from different plant sources, high amylase and high amylopectin varieties. The term "starch," as used herein, also includes water-soluble film-forming polymer materials derived from starch, including starch derivatives such as starch hydrolate products, modified starches, modified starch derivatives, and maltodextrins. Water soluble carbohydrate oligomers are preferred. Suitable water soluble carbohydrate oligomers include xylose, ribose, glucose, mannose, galactose, fructose, dextrose, polydextrose, sucrose, maltose, corn syrup solids, palatin, sorbitol, xylitol, mannitol, maltitol, lactitol, xanthan, maltodextrin, galactomanan, tragacanth, manitol, lactitol, oligisaccharides and hydrocolloids, and mixtures thereof, such as corn syrup, honey, high fructose corn syrup, etc.

In an embodiment of the present invention in which the self-supporting adhesive film is formed with corn syrup containing a mixture of water soluble carbohydrates of glucose and its polymers, the adhesive properties of the film are generally tied to the moisture content of the substance in which the water soluble carbohydrates is contained. In such embodiment, the film structure preferably has a moisture content in the range of about 6% to about 15% by weight to provide adequate adhesion. Below such range typically does not provide sufficient adhesion, and above such range typically causes the film to lose too much structure.

In one embodiment, polysaccharides can be used. Suitable polysaccharides are polysaccharides of the non-sweet, colloidally-soluble types, such as natural gums, for example, gum arabic, starch derivatives, dextrinized and hydrolyzed starches, and the like. A suitable polysaccharide is a water-dispersible, modified starch.

In one embodiment, water soluble bioadhesive polymers can be used for enhancing skin adhesive property. Examples useful for the invention include, but are not limited to, cellulose and its derivatives, polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester, polyethylene glycol, water soluble acrylic polymers, water soluble polyesters, hydroxyalkyl starches, casein, gelatin, solubilized proteins, polyacrylamide, polyamines, polyquarternium amines, styrene maleic anhydride resins, polyethylene amines, The water soluble carbohydrate can form hydrogen or covalent bonding to the water soluble or hydrophilic polymer in the film.

In accordance with one aspect of the present invention, the adhesive quality of self-supporting adhesive films 100 and 200 of the present invention are preferably capable of fixing the self-supporting adhesive film to the skin of a user for an extended period of time, as discussed herein above, without irritating the skin. Preferably, the self-supporting adhesive film is capable of adhering to the application site for as long as reasonable and/or indicated to have a self-supporting adhesive film in place at such site. Thus, an upper temporal limit to adhesion time is not important, since the user or wearer typically will want to remove the self-supporting adhesive film before the self-supporting adhesive film would naturally wear off of the application site on its own. Typically, the amount of time a self-supporting adhesive film of the present invention is to adhere to a given application site is dictated by the amount of time the application area can withstand not being exposed to water. For instance, it will be appreciated that some surgical sites are not to be exposed to water for extended periods of time, such as several days. Self-supporting adhesive film for application to such sites should accordingly be capable of adhering to such site for so long as the site is not exposed to water, if desired. As may be appreciated, the adhesive preferably is selected for application onto a skin surface which typically is not considered to be moist, in contrast with mucosal tissue. It will be appreciated that by being capable of adhering to the user's skin, the self-supporting adhesive film simply is capable of adhering, but need not necessarily adhere if such property is not desired or unnecessary for a particular application.

Because self-supporting adhesive films 100 and 200 of the present invention preferably are formed to remain adhered to the application site for an extended period of time, as described above, non skin-contacting surface 114 and top surface 224 of first embodiment film structure 100 and second embodiment film structure 200, respectively, preferably have desirable properties and features to facilitate such an intended use of the self-supporting adhesive film. For instance, because a self-supporting adhesive film or surface is designed to adhere to an application site, if the self-supporting adhesive film is designed to adhere to an application site for an extended period of time, then an adhesive outwardly-facing surface may unintentionally or inadvertently adhere to another surface or object during use of the self-supporting adhesive film. Such unintentional or inadvertent occurrence may cause the self-supporting adhesive film to become dislodged, or, worse, disengaged (partially or even fully) from the application site. Moreover, it will be appreciated that an adhesive material typically attracts dust or dirt or other debris, which would likely be considered by the wearer to be unsightly and undesirable. Accordingly, it is preferable that surfaces 114 and 224 of the present invention are non-tacky; not adhesive. Thus, self-supporting adhesive films 100 and 200 of the present invention, to remain adhered to an application site for an extended period of time, preferably surfaces 114 and 224 that are non-tacky; non-adhesive.

If surfaces 114 or 224 rub against or are rubbed by something or otherwise contacts or is contacted by another surface or self-supporting adhesive film, the self-supporting adhesive films 100 and 200 should not adhere to such surface or film structure.

Self-supporting adhesive films 100 and 200 may be tinted or pigmented to match the skin tone of the user so to be aesthetically pleasing, or at least not unaesthetic or unsightly, when worn.

Self-supporting adhesive films 100 and 200 may be formed to be clear to be discrete in situ. Further properties may be selected to render self-supporting adhesive films 100 and 200 of the present invention visually discrete when in situ so that if the self-supporting adhesive film is worn during the day its noticeability is minimized as much as possible. For instance, the thinner the self-supporting adhesive film is, the less visible the film structure typically is. In addition, or alternatively, the color, texture (e.g., rough, slick, smooth, or otherwise textured such as an "orange peel" surface to match substantially the texture of the skin to which the self-supporting adhesive film is applied so that the self-supporting adhesive film is not starkly smooth relative to the skin with its natural imperfections), shine (shiny or dull depending on application site), etc., may be modified as desired to facilitate blending in of the self-supporting adhesive film with the application site. Because self-supporting adhesive films 100 and 200 of the present invention may be configured to be worn for an extended period of time (e.g., more than an hour, such as described above, and/or even overnight), the self-supporting adhesive film preferably is formed or configured to be comfortable when worn. A variety of factors (individually or in any combination) may be considered in achieving the desired comfort and level of comfort, including, without limitation, tactile properties, material thickness (affecting not only durability, but also weight on the application site), and stiffness. Tactile properties that may contribute to comfort include smoothness, and/or stickiness of the adhesive used to adhere the film structure to a selected application site, etc. Additional tactile properties that may contribute to comfort include softness, smoothness, and texture of the film, such as determined by modulus of elasticity and coefficient of friction (rather than merely the aesthetic aspects of such properties).

Thickness affects a variety of additional factors, including stiffness—a stiffer self-supporting adhesive film typically being less comfortable than a less stiff self-supporting adhesive film. Material properties (a function of the composition of the material, independent of form) as well as structural properties (the form of the self-supporting adhesive film) may affect the achievable comfort level of a self-supporting adhesive film used in accordance with principles of the present invention when worn by a user. It will be appreciated that all the desired properties for a self-supporting adhesive film used in accordance with principles of the present invention must be balanced, wherein some properties complementary, yet others have opposing dimensions. With regard to comfort, it will be appreciated that properties contributing to comfort must be balanced with properties contributing to structural integrity. There are at least three structural properties that affect "comfort": flexibility (about a single, bending direction; generally, flexibility is considered a combination of thickness and flexural modulus), stretchability (in a single axial direction; generally, stretchability is considered a combination of thickness and elastic modulus), and conformability (generally considered a combination of flexibility and physical shape in multiple directions, about complex surface). Comfort may be achieved by minimizing both the thickness and the elastic modulus. It will be appreciated that flexibility and stretchability are both functions of the elastic modulus of the material. More particularly, flexibility generally is dictated by the thickness of the material as well as the flexural modulus. Stretchability is a function of thickness and elastic modulus. When the material is thicker, stiffness increases (which property correlates with comfort) and flexibility and stretchability are reduced, generally adversely impacting comfort. The elastic modulus generally affects how rubbery or brittle a material is, and is tied to comfort because it determines flexibility of the material. Increasing the flexural or elastic modulus of a material makes the material less flexible or stretchable, respectively. Specifically, a higher flexural or elastic modulus results in a stiffer material, so the material consequently is less flexible and less stretchable. Given a constant flexural or elastic modulus, a higher material thickness will make the material less flexible or stretchable. As may be appreciated, comfort may be achieved by minimizing thickness of a given film to the lowest practical limit. The lower limit is dictated by providing enough structure to handle and manipulate the self-supporting adhesive film and to facilitate application and removal of the self-supporting adhesive film. From a material standpoint, the elastic modulus is most strongly linked to comfort. The lower the elastic modulus, the more comfortable the film structure typically is. An elastic modulus of from about 500 psi to about 10,000 psi provides an acceptable degree of comfort for a user, with a more preferred range of elastic modulus of from about 1,000 psi to about 5,000 psi, with a preferred elastic modulus of about 2,500 psi. Conformability, such as the ability to conform to a given site (typically a surface with a complex curvature), not only involves flexibility, in general, but also relates to multidirectional flexibility and stretchability (e.g., so the self-supporting adhesive film may stretch if placed over a joint). Conformability generally must be defined in terms of the physical shape or contour of the application site, and is determined with respect to a surface in conjunction with flexibility. A self-supporting adhesive film may need to have a particular planar shape to be able to conform to a complex surface. Preferably, a self-supporting adhesive film used in accordance with principles of the present invention has substantially the same properties in all directions.

If self-supporting adhesive films 100 and 200 used in accordance with principles of the present invention are to remain on the application site for an extended period of time, such self-supporting adhesive film preferably has a desired degree of breathability. Breathability may also be important for obtaining desired skin moisturization or proper skin moisture content balance for the functionality of the self-supporting adhesive film in providing such benefit. Breathability relates to and is a function of oxygen exchange, which affects skin barrier as well as consumer perception. Breathability also is a function of water transmission. Self-supporting adhesive films 100 and 200 used in accordance with principles of the present invention preferably are sufficiently breathable so that the skin moisture content remains balanced. Of course, if one of the desired outcomes of use of the present invention is to improve or to increase skin moisture content, then the breathability of the self-supporting adhesive film preferably may be selected to facilitate such moisturization, as discussed in further detail below. A semi-occlusive film will at least partially inhibit water loss and therefore hold moisture within the skin. Self-supporting adhesive films 100 and 200 used in accordance with principles of the present invention preferably provides resistance to moisture transmission, and may have a moisture transmission rate of approximately 50-150 grams of water per hour per square meter. Such self-supporting adhesive film has been found to block or occlude evaporation that would occur without a film barrier by approximately 87%.

Self-supporting adhesive films 100 and 200 used in accordance with principles of the invention, as further described below, may be semi-occlusive (preferably approximately 85% occlusive) not only to maintain breathability, but also to provide other benefits discovered to result from covering the application site with a semi-occlusive self-supporting adhesive film. In second embodiment self-supporting adhesive film 200 of the present invention, top layer 220 may further contribute to the overall semi-occlusive nature of the self-supporting adhesive film. In particular, a top layer 220 may function in conjunction with a hygroscopic skin-contacting layer 210. Once such a skin-contacting layer hydrates further, it may further lose structural integrity, and transform from a film-type substance to a gel phase without structural integrity independent of top layer 220. Top layer 220 thus essentially caps and contains the skin-contacting surface at the application site so that the skin-contacting surface can hydrate the application site.

Self-supporting adhesive films 100 and 200 used in accordance with principles of the present invention dissolve or disintegrate with only the addition of water. Preferably, no mechanical agitation is required to facilitate the removal of the self-supporting adhesive film. Preferably, self-supporting adhesive films 100 and 200 used in the present invention preferably completely dissolves within the parameters of a typical consumer washing regimen for the application site if no self-supporting adhesive film is present, so no additional washing time is required by the consumer. Preferably, self-supporting adhesive films 100 and 200 used in the present invention are quick-dissolving for ready removal from the application site on the user (when washing one's face, preferably less than about 5 minutes, and even less than about 1 minute, and even about 30 seconds after addition of a water thereto). It will be appreciated that a longer dissolution rate is acceptable for sites on other parts of the body that are typically washed for more than 5 minutes, but preferably not so long a dissolution time that scrubbing is required to achieve removal). With simulated cleansing water flow of about 4 feet/sec (parallel flow to surface of film), complete dissolution was measured in about 67 seconds with initial breach of the outer film surface occurring at about 30 seconds. In another embodiment, the film can be removed with a wet cloth, sheet, or pad made of woven or nonwoven materials.

The primary mechanical strength of the film is created by the film former (preferably polyvinyl alcohol (PVA)), which typically is also selected based on its ability to permit ready breakdown of the self-supporting adhesive film as desired. It will be appreciated that in one embodiment, the film former preferably is selected to achieve the desired ability to dissolve or disintegrate the self-supporting adhesive film for removal upon application of water thereto, and may be the first component of the self-supporting adhesive film composition that is selected, other components being selected to interact as desired with the already-selected film former. Flexibility is achieved by the addition of a plasticizer, such as glycerin, to the film former. Film formers and/or plasticizers typically are the primary contributors to structural integrity, and are typically a component of the composition used to form the outwardly-facing top layer with properties such as described above. Exemplary film formers and plasticizers are set forth in greater detail below. Looking at solids content, PVA can be 70% by weight of the dry ingredients of a film structure used in accordance with principles of the present invention, with glycerin at 20% by weight. The glycerin can range from as little as 10% to 30% by weight of the film structure, and the PVA can be as much as 90% by weight of the dry ingredients.

The hydrophilic film-forming polymers suitable for producing the topical skin self-supporting adhesive films 100 and 200 used in the present invention may be of synthetic, semisynthetic, or natural origin. Such hydrophilic film forming polymers include, without limitation, cellulose ethers, polyvinyl alcohols, polyvinyl acetate, polyvinyl pyrrolidone, polysaccharides, as well as derivatives, copolymers or polymers thereof. The multi-layer topical skin self-supporting adhesive film may be made into a wide variety of product forms that include but are not limited to the form films.

In one embodiment, adhesion of a self-supporting adhesive film of the present invention is achieved by provision of invertase, or corn syrup (preferably high fructose corn syrup) as an ingredient of the self-supporting adhesive film. The corn syrup, combined with residual moisture remaining in the film after drying, causes the self-supporting adhesive film to exhibit the desired adhesive properties and imparts the adhesive quality to the self-supporting adhesive film.

Exemplary methods of forming one-layer film structures of the present invention are discussed in United States Patent Applications Publication Nos. US2015/0182991A1 (Ser. No. 14/580,974), entitled "PROCESS FOR FORMING AN INTEGRAL FILM PRODUCT", filed on Dec. 23, 2014, and US2015/0182993A1 (Ser. No. 14/581,010), entitled "PROCESS FOR FORMING A SHAPED FILM PRODUCT", filed on Dec. 23, 2014, both of which publications are incorporated by reference herein in their entireties.

Exemplary methods of forming two-layer self-supporting adhesive film of the present invention are discussed in United States Patent Applications Publication Nos. US2015/0182992A1 (Ser. No. 14/580,977), entitled "PROCESS FOR FORMING A MULTILAYERED SHAPED FILM PRODUCT", filed on Dec. 23, 2014, and US2015/0182990A1 (Ser. No. 14/581,057), entitled "SINGLE-PASS PROCESS FOR FORMING A MULTILAYERED SHAPED FILM PRODUCT", filed on Dec. 23, 2014, both of which publications are incorporated by reference herein in their entireties.

A self-supporting adhesive film may be formed in accordance with one embodiment of the present invention by casting and drying skin-contacting layer 210, and then casting top layer 220 on top of skin-contacting layer 210. The two layers adhere to one another by any of the known methods of adhesion (mechanical, chemical, dispersive, electrostatic, diffusive, etc.). In one embodiment, the two layers preferably are both water soluble, so that the water in the nonadhesive top layer 220 will slightly dissolve the already dried skin-contacting layer 210, thereby creating a certain amount of diffusive adhesion at the interface of the two layers. In a second embodiment of the present invention, both layers are cast wet on wet, and intermixing of the materials occurs at the interface therebetween, thereby creating a bond by diffusive adhesion. Preferably, the materials have a common solvent and/or are miscible with each other so that they intermix and bond together. It will be appreciated that the materials of the top layer 220 and skin-contacting layer 210, could have a common solvent other than water, such as alcohol, so that the materials bond to each other.

The self-supporting adhesive films 100 and 200 of the present invention may contain at least one active substance, or active agent. The active agents that may be used in film structures of the invention include cosmetic agents and therapeutic agents. As used herein, benefitting agent means an ingredient or material that provides a benefit, e.g., improves, relieves, reduces, or treats symptoms or conditions of the skin, ether cosmetic or therapeutic. Such substances may be any of a variety of compositions, including, without limitation, hyaluronic acid; hydroxyl acids (e.g., glycolic acid, lactic acid, malic acid, salicylic acid, citric acid, tartaric acid); anti-acne agents (e.g., salicylic acid, retinol, retinoids, or other keratolytics, and benzoyl peroxide, or other antimicrobial agents used to treat acne); shine control agents (e.g., rice protein, cotton powder, elubiol (dichlorophenyl-imidazoltioxolan); a retinoid or its derivative such as tretinoin, isotretinoin, motretinide, adapalene, tazarotene, azelaic acid, and retinol; a 5-alpha-reductase inhibitor of amino acids, e.g., glycine derivatives; hydrolyzed vegetable proteins, including soy protein and wheat protein, etc.; green tea (*camellia sinesis*) extract, and cinnamon bark extract); moisturizers; anti-microbial agents (e.g., cationic antimicrobials such as benzylkonium chloride, benzethonium chloride, triclocarbon, polyhexamethylene biguanide, cetylpyridium chloride, methyl and benzothonium chloride; salts of chlorhexidine, such as lodopropynyl butylcarbamate, diazolidinyl urea, chlorhexidene digluconate, chlorhexidene acetate, chlorhexidine isethionate, and chlorhexidene hydrochloride; halogenated phenolic compounds, such as 2,4,4'-trichloro-2-hydroxy diphenyl ether (Triclosan); parachlorometa xylenol (PCMX); short chain alcohols, such as ethanol, propanol, and the like); antibiotics or antiseptics (mupirocin, neomycin sulfate bacitracin, polymyxin B, 1-ofloxacin, tetracyclines (chlortetracycline hydrochloride, oxytetracycline-10hydrochloride and tetrachcycline hydrochoride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs), anti-inflammatory agents (e.g., suitable steroidal anti-inflammatory agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinol one acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluorometha-lone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts, nonsteroidal anti-inflammatory agents, feverfew (*Tanacetum parthenium*), goji berry (*Lycium barbarum*), milk thistle extract (*Silybum marianum*), amaranth oil (*Amaranthus cruentus*), pomegranate (*Punica granatum*), yerbe mate (*Ilex paraguariensis* leaf extract), white lily flower extract (*Lilium Candidum*), olive leaf extract (*Olea europaea*) and phloretin (apple extract)); antimycotic/antifungal agents (e.g., miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs; an azole, an allylamine, or a mixture thereof); external analgesics (e.g., ibuprofen- or diclofenac; capsaicin, fentanyl, and salts thereof such fentanyl citrate; paracetamol (as acetaminophen); non-steroidal anti-inflammatory drugs (NSAIDs) such as salicylates; opioid drugs such as morphine and oxycodone; ibuprofen- or diclofenac-containing gel); antioxidants (e.g., sulfhydryl compounds and their derivatives (e.g., sodium metabisulfite and N-acetyl cysteine), lipoic acid and dihydrolipoic acid, resveratrol, lactoferrin; ascorbic acid, ascorbic acid esters, and ascorbic acid derivatives (e.g., ascorbyl palmitate and ascorbyl polypeptide); butylhydroxy anisole, butylated hydroxytoluene (butylhydroxy toluene), retinoids (e.g., retinol and retinyl palmitate), tocopherols (e.g., tocopherol acetate), tocotrienols, and ubiquinone; cysteine, N-acetylcysteine, sodium bisulfite, sodium metabisulfite, sodium formaldehydesulfoxylate, acetone sodium bisulfite, tocopherols, and nordihydroguaiaretic acid; extracts containing flavonoids and isoflavonoids and their derivatives (e.g., genistein and diadzein); extracts containing resveratrol and the like; grape seed, green tea, pine bark, and propolis; plant-derived polyphenol antioxidants such as clove, cinnamon, oregano, turmeric, cumin, parsley, basil, curry powder, mustard seed, ginger, pepper, chili powder, paprika, garlic, coriander, onion and cardamom; typical herbs such as sage, thyme, marjoram, tarragon, peppermint, oregano, savory, basil and dill weed)); depilatory agents (e.g., calcium thioglycolate or potassium thioglycolate); vitamins (e.g., Vitamin A, Vitamin B, Vitamins C, Vitamin E; either alpha, beta, gamma or delta tocopherols, niacin or niacinamide) and vitamin salts or derivatives such as ascorbic acid diglucoside and vitamin E acetate or palmitate; sunblock (e.g., titanium dioxide) and/or sunscreen (e.g., inorganic sunscreens such as titanium dioxide and zinc oxide; organic sunscreens such as octyl-methoxy cinnamates, octyl salicylate, homosalate, avobenzone); vasodilators (e.g., niacin); humectants (e.g., glycerin); anti-aging agents (e.g., retinoids; dimethylaminoethanol (DMAE), copper containing peptides); alpha hydroxy acids or fruit acids and their precursors such as glycolic acid, citric acid, lactic acid, malic acid, mandelic acid, ascorbic acid, alpha-hydroxybutyric acid, alpha-hydroxyisobutyric acid, alphahydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; botanical extracts such as green tea, soy, milk thistle, algae, aloe, *angelica*, bitter orange, coffee, goldthread, grapefruit, hoellen, honeysuckle, Job's tears, lithospermum, mulberry, peony, puerarua, nice, and safflower, and salts and prodrugs thereof); carotenoids, ceramides, fatty acids, enzymes, enzyme inhibitors, minerals, steroids, peptides, amino acids, botanical extracts, colorants, etc. The substances may affect the skin in any of a variety of manners, such as by moisturizing; enhancing skin tone or color (such as with pigments); treating or at least mitigating various skin conditions (such as dry or severe dry skin, eczema, psoriasis, atopic dermatitis, allergic rashes, acne, blackheads, pustules, comedones, rosacea, shingles, wrinkles, cold sores, herpes, corns, warts, sunburn, insect bites, poison ivy, etc.); applying a mechanical force to smooth wrinkles; or, more generally, treating or mitigating the symptoms and appearance of undesired skin imperfections (such as under eye dark circle, redness of acne, fine lines and wrinkles, post inflammatory hyperpigmentation (PIH), redness, inflammation, cellulite, wrinkles, age spots, mottled pigmentation, dark spots, liver spots, under eye puffiness); removing unwanted facial or body hair; aiding in wound healing; etc. For instance, lotions, creams, oils, and even masks may be applied to skin to treat or otherwise to affect the skin. Such personal or consumer healthcare substances are absorbed into the skin generally following the principles of diffusion, under which the rate of diffusion or transport across the skin is correlated with the difference in active concentration on both sides of the skin.

As mentioned above, combinations of cosmetic formulations and electrically powered stimulations have been found to be useful in the treatment of some cosmetic flaws. Electrically powered stimulations can enhance the effect of the active substances in self-supporting topical adhesive films 100 and 200. Stimulation can be in the form of light, heat, cooling, or vibration.

Embodiments of electrically powered patch 10 and self-supporting adhesive films 100 and 200 of the present invention will be used in the following manner to enhance the effect of the active substances in the treatment of cosmetic flaws.

In one embodiment, first embodiment self-supporting adhesive film 100 of the present invention is disposed on the skin of a consumer at the site in need of treatment. Skin-contacting surface 112 of self-supporting adhesive film 100 adheres to the user's skin. Next, the major surface of an electrically powered patch embodiment 10 is releasably attached to the exposed surface 114 of self-supporting adhesive film 100. This releasable attachment to first (major) surface 22 of electrically powered patch 10 has sufficient attachment strength to prevent separation of the self-supporting adhesive film 100 from electrically powered patch 10 during routine movements of the skin.

In some embodiments, a user may purchase a kit containing electrically powered patch 10 with one or more separately packed self-supporting adhesive film 100. Kits may contain one or more electrically powered patches 10, as well as one or more, two or more, five or more, or ten or more substance containing self-supporting adhesive film 100. In some embodiments, substance containing self-supporting adhesive film 100 may be packed in air-tight packs to prevent loss of active from film structure 100. In other embodiments, there may be release liner disposed on one or both of non skin-contacting surface 114 and skin-contacting surface 112 to protect the surface(s) prior to use.

In other embodiments, electrically powered patch 10 and self-supporting adhesive films 100 and 200 of the present invention may be pre-combined to create a skin treatment device prior to use. Referring to FIG. 5, a side view of a skin treatment device 60 comprised of electrically powered patch embodiment 10 in combination with first embodiment of an active substance containing self-supporting adhesive film 100 prior to being disposed on the skin of a consumer at the site in need of treatment. Here, active substance containing self-supporting adhesive film 100 is disposed on first (major) surface 22 of electrically powered patch 10. Non skin-contacting surface 114 of self-supporting adhesive film 100 adheres to first surface 22 of electrically powered patch 10 with sufficient adhesion so as to prevent separation of self-supporting adhesive film 100 from electrically powered patch 10 during routine manipulation of device 60.

In some embodiments, skin treatment device 60 is purchased as a pre-assembled device with self-supporting adhesive film 100 predisposed on first surface 22 of electrically powered patch 10. In these embodiments, skin treatment device 60 may be viewed as a one-time use skin treatment device. In some embodiments, there may be a release liner disposed on skin-contacting surface 112 of skin treatment device 60 to protect the surface prior to use.

In other embodiments, a user may purchase a kit containing electrically powered patch 10 with one or more separately packed self-supporting adhesive films 100. In these embodiments, the user assembles skin treatment device 60 by releasably attaching a self-supporting adhesive film 100 on first (major) surface 22 of electrically powered patch 10 to prepare device 60 for use. The tacky adhesive surface of the self-supporting adhesive film is then applied to the isolated body part, such as skin or mucosal membrane. Kits may contain one or more electrically powered patches 10, as well as one or more, two or more, five or more, or ten or more substance containing self-supporting adhesive films 100. In some embodiments, substance containing self-supporting adhesive films 100 may be packed in air-tight packs to prevent loss of active from self-supporting adhesive film 100. In other embodiments, there may be release liner disposed on one or both of non skin-contacting surface 114 and skin-contacting surface 112 to protect the surface(s) prior to use.

In some embodiments, kits may contain one or more pre-assembled skin treatment device 60 with self-supporting adhesive film 100 predisposed on first surface 22 of electrically powered patch 10, with one or more additional separately packed self-supporting adhesive films 100. Once skin treatment device 60 is ready, user applies the device to the site of treatment. FIG. 6 is a side view of skin treatment device 60 disposed on the skin 150 of a consumer. Skin-contacting surface 112 of skin treatment device 60 adheres to the skin surface 152 at the treatment site. The adhesive quality of skin treatment device 60 of the present invention are preferably capable of fixing device 60 to the skin of a user for an extended period of time, as discussed herein, without irritating the skin. Preferably, device 60 is capable of adhering to the application site for as long as reasonable and/or indicated to have such device 60 in place at such site.

In embodiments where skin treatment device 60 is purchased as a pre-assembled device with self-supporting adhesive film 100 predisposed on first surface 22 of electrically powered patch 10, user directly applies skin treatment device 60 on skin surface 152 at the treatment site. If device 60 has a release liner disposed on skin-contacting surface 112 of skin treatment device 60, user removes release liner prior to applying device 60 on skin surface 152.

In embodiments where skin treatment device 60 is purchased as a kit containing electrically powered patch 10 with one or more separately packed self-supporting adhesive films 100, user first assembles device 60 by disposing active substance containing self-supporting adhesive films 100 on first surface 22 of patch 10, preparing device 60 for use. Prepared device 60 is then applied to skin surface 152 at the treatment site. If self-supporting adhesive film 100 has release liner(s) disposed on non skin-contacting surface 114 and/or skin-contacting surface 112, user removes release liner(s) prior to assembling device 60.

Next, user initiates the electrically powered patch treatment cycle, energizing the active element(s). This can be accomplished, for example, by the user pressing and on/off switch located on electrically powered patch 10. Treatment cycles can use light, heat, cooling, vibration, or combinations thereof. The length of the treatment cycle will depend on skin flaw being treated and the active substance being used. In some embodiments, patch treatment cycle is less than sixty (60) minutes, or thirty (30) minutes, or ten (10) minutes, or five (5) minutes, or one (1) minute.

The treatment cycle is next completed. In some embodiments, the user manually completes the cycle by, for example, pressing an on/off switch located on electrically powered patch 10. In other embodiments, electrically powered patch 10 has a timing mechanism, and device 60 will shut down upon completion of the treatment cycle.

Figure 7:
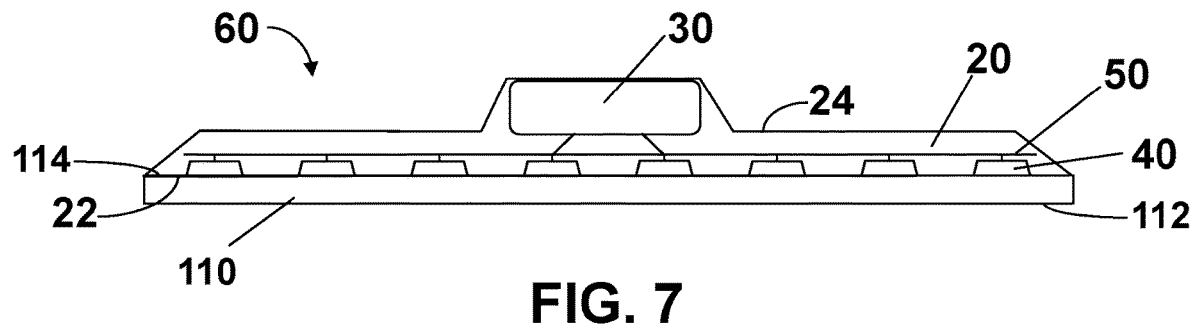
FIG. 7 is a side schematic view of a skin treatment device comprised of an electrically powered patch embodiment of FIG. 1 in combination with a first embodiment of a self-supporting adhesive film portion of the present invention prior to being placed on the skin of a consumer.
Figure 8:
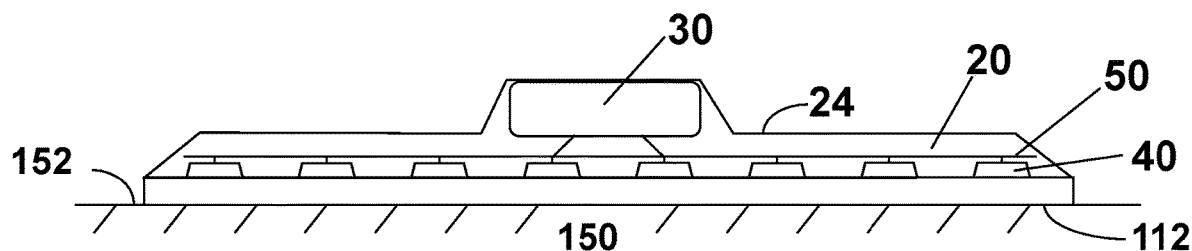
FIG. 8 is a side schematic view of the device of FIG. 7 disposed on the skin of a consumer.
Figure 9:
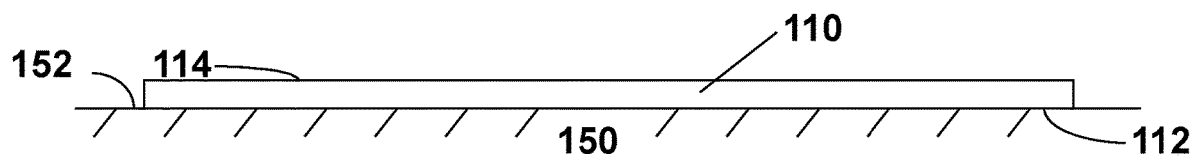
FIG. 9 is a side schematic view of the self-supporting adhesive film portion of the device after the electrically powered patch portion of the device has been removed from the self-supporting adhesive film portion of the device.

Next, electrically powered patch 10 is separated from active substance containing self-supporting adhesive film 100, leaving self-supporting adhesive film 100 adhered to skin surface 152 at the treatment site. Self-supporting adhesive film 100 remains adhered to skin surface 152 when electrically powered patch 10 is removed because the adherence of electrically powered patch 10 to self-supporting adhesive film 100 is less than the adherence of film structure 100 to skin. FIG. 7 is a side view of the active substance containing self-supporting adhesive film 100 portion of device 60 after the electrically powered patch portion 10 has been removed from treatment site.

Self-supporting adhesive film 100 can now be left at the site of treatment for an extended time period. The extended time period can be used to further deliver active substance to the treatment site, or to protect the treatment site. Self-supporting adhesive film 100 stays on the site of treatment for at least 1 minute, or at least 5 minutes, or at least 15 minutes, or at least half an hour, or at least one hour, or at least about six (6) to eight (8) hours, or at least about twelve (12) hours, or about twenty four (24) hours. In some embodiments, the consumer removes self-supporting adhesive film 100 manually, by peeling, for example. In other embodiments, self-supporting adhesive film 100 is readily removable upon application of water thereto. By readily removable, it is meant that the self-supporting adhesive film may dissolve or disintegrate upon application of water to the self-supporting adhesive film, such that it may be removed from the skin without scrubbing, or the like. In the event that the skin treatment device includes a plurality of electrically connected patches, as described below, the foregoing steps would be repeated for each such patch.

Figure 10:
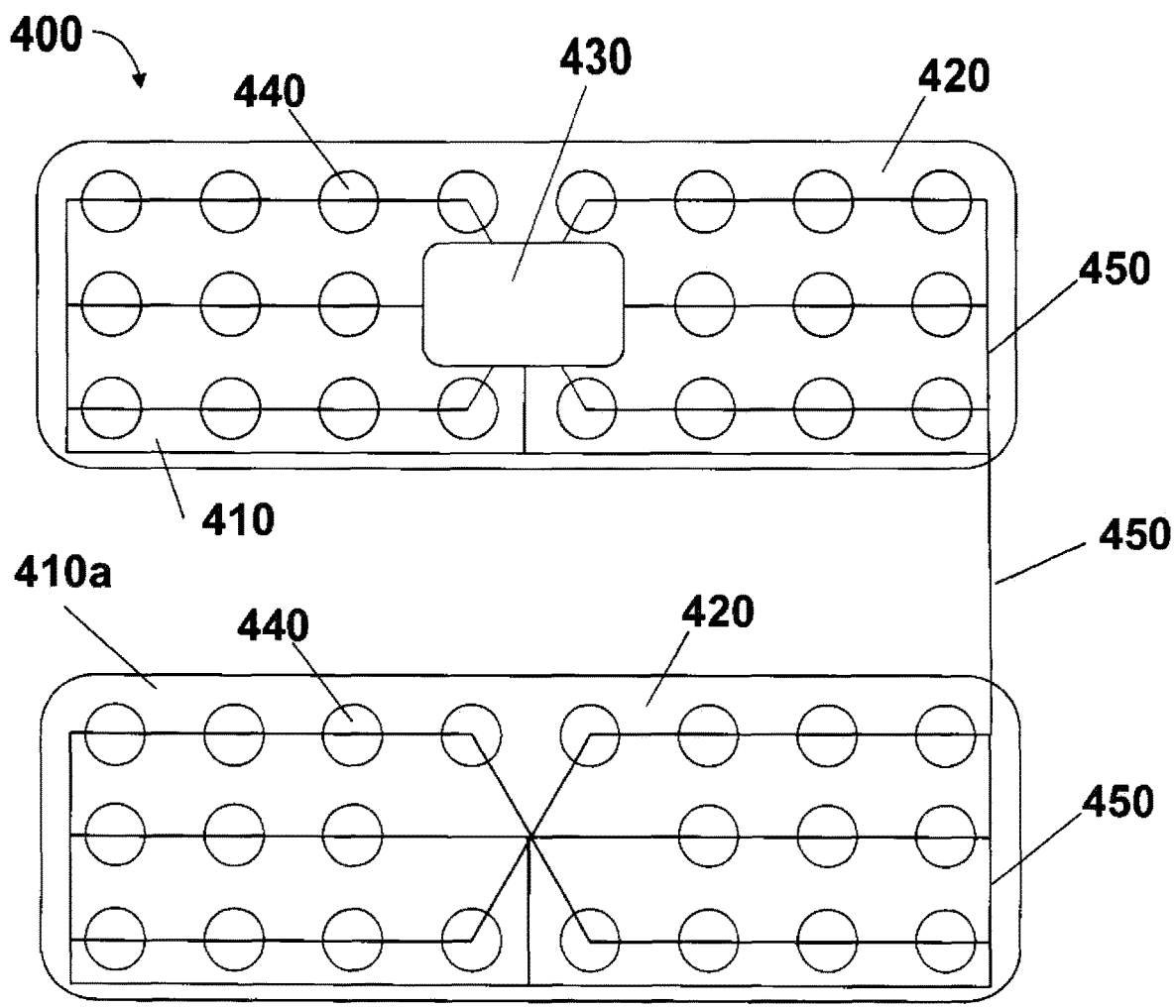
FIG. 10 is a top schematic view of an alternative embodiment of an electrically powered patch system having a plurality of electrical patches.

While the foregoing description has referenced a system having a single electrically powered patch, an alternative embodiment includes a plurality of electrically connected patches. FIG. 10 shows an example of such a system 400. The system 400 includes a master electrically powered patch 410 and a connected slave patch 410a. Again, each electrically powered patch 410, 410a includes a matrix 420 and active elements 440 interconnected by conductor 450, which also connects the several electrically powered patches, 410, 410a. One electrically powered patch 410 also has a controller, such as a control panel 430, which has associated therewith a power source.

Additional electrically connected patches 410b . . . 410n may be incorporated with the system described in the foregoing description.

EXAMPLES

The present invention will be further understood by reference to the following specific Example which is illustrative of the composition, form and method of producing the present invention. It is to be understood that many variations of composition, form and method of producing this would be apparent to those skilled in the art. The following Examples, wherein parts and percentages are by weight unless otherwise indicated, are only illustrative.

Example 1: Device 60 for Anti-Aging Treatment

An anti-aging prototype skin treatment device was constructed comprising an electrically powered patch embodiment 10 in combination with an embodiment of an active substance containing self-supporting adhesive film 200.

The electrically powered patch embodiment 10 contained the following electronic components: Light Emitting Diodes (SunLED XZM2ACR105S), Battery (GM300910HB), LED driver circuit, and microprocessor (Nordic Semiconductor, NRF51822-CFAC-R). The components were encapsulated in a silicone matrix 20 of the formulation shown in Table 1.

TABLE 1

Formulation for Silicone Matrix.

| Ingredients | Weight (g) | Weight % |
| --- | --- | --- |
| SORTA-CLEAR 18 resin | 50 | 76.9 |
| SORTA-CLEAR 18 hardener | 5 | 7.7 |
| SLACKER | 10 | 15.4 |
| TOTAL | 65 | 100.0 |

Encapsulation was as follows:
1. A mold was fabricated to represent the bottom half of the finished patch, using the formulation as indicated above. After filing the mold, the silicone was cured at 60° C. for 2 hours.
2. After demolding the bottom half, the electronic assembly, and the cured bottom section, was placed into an open second mold.
3. The open mold containing the first half and the electronics was then filed with the liquid silicone and the mold was closed. The closed mold represents the final light patch shape, with the electronics assembly located along the center plane of the finished patch.
4. Step 4: The second layer of silicone was then cured once more at 70° C. for 2 hours.

Self-supporting adhesive film 200 was formed with a top layer 220 and a skin-contacting layer 210. The formulation for the top layer 220 is shown in Table 2.

TABLE 2

Formulation for Top Layer.
Notebook #12924, Page #120

| Ingredients | Weight (g) | Solid % (in film) | % In Solution | Lab Batch (g) |
| --- | --- | --- | --- | --- |
| Selvol 805 | 22.9730 | 80.7543 | 27.2037 | 190.43 |
| Polysorbate 80 | 1.7500 | 6.1516 | 2.0723 | 14.51 |
| Dow Corning 2501 Cosmetic Wax | 0.8000 | 2.8112 | 0.9473 | 6.63 |
| Kester Wax K-24 | 0.8000 | 2. 8122 | 0.9473 | 6.63 |
| Glycerin 99.7%, USP | 2.1250 | 7.4698 | 2.5163 | 17.61 |
| Water, Purified | 56.0000 | | 66.3130 | 464.19 |
| | | 100.0000 | 100.0000 | |
| Total Solid Weight (g) | 28.4480 | | | 235.81 |
| Total Batch Weight (g) | 84.4480 | | | 700.0000 |
| % Solid | 33.69 | | | |

The formulation for skin-contacting layer 210 is shown in Table 3.

TABLE 3

Formulation for Skin-Contacting Layer.
Notebook #13237, Page #129

| Ingredients | Weight (g) | Solid % (in film) | % In Solution | Lab Batch (g) |
|---|---|---|---|---|
| Plasdone K-29/32 | 17.8240 | 43.3448 | 20.2266 | 70.7932 |
| Plasdone S-630 | 4.4560 | 10.8362 | 5.0567 | 17.6983 |
| Glycerox 767 | 1.0000 | 2.4318 | 1.1348 | 3.9718 |
| Cosmedia SP | 0.7500 | 1.8239 | 0.8511 | 2.9788 |
| Glycerin, USP 99.7% | 7.3297 | 17.8245 | 8.3177 | 29.1121 |
| Monomuls 90-O18 | 2.0561 | 5.0001 | 2.3333 | 8.1664 |
| Hexylresorcinol | 0.2056 | 0.5000 | 0.2333 | 0.8166 |
| Invertose HFCS 26550 (Ingredion) | 7.5000 | 18.2387 | 8.5110 | 29.7558 |
| Water, Purified | 47.0000 | | 53.3355 | 186.7643 |
| | | 100.0000 | 100.0000 | |
| Total Solid Weight (g) | 41.1214 | | | 163.3257 |
| Total Batch Weight (g) | 88.1214 | | | 350.0000 |
| % Solid | 46.66 | | | |

The self-supporting adhesive film 200 was made using a film casting method of the following steps:

1. A first layer was created by pouring 20 grams of the skin-contacting formulation onto a siliconized release paper.
2. A casting bar with a clearance of 0.004 inch was used to draw the liquid formulation along the top of the release liner to create a 0.004-inch thick layer of liquid formulation.
3. This first layer was then cured in a convective hot air oven at 70° C. for 12 minutes.
4. After drying the first layer, 20 grams of the top layer formulation was poured along one edge of the first layer.
5. A casting bar with a clearance of 0.006 inches was used to draw the liquid into a thin film over the first layer with a wet thickness of 0.004 inches.
6. This was then dried in a hot air oven at 70° C. for 12 minutes.
7. The dried double layer film was then cut with a die, to match shape of the silicone light patch To complete the assembly of the prototype skin treatment device for anti-aging, the electrically powered patch was disposed on the active substance containing self-supporting adhesive film by hand, and slight pressure was used to removably attach the two elements together.

The anti-aging prototype skin treatment device was then disposed on the face of a human subject to verify that it would adhere to the subject's skin. After several minutes, the electrically powered patch was separated from the active substance containing self-supporting adhesive film, leaving the active substance containing self-supporting adhesive film disposed on the face of the human subject.

Example 2: Formulation for Anti-Aging Treatment

A self-supporting adhesive film, made according to the process above was formed with a top layer (Table 4) and bottom layer (Table 5):

TABLE 4

Formulation for Top Layer.
Notebook #13237, Page #139

| Ingredients | Weight (g) | Solid % (in film) | % In Solution | Lab Batch (g) |
|---|---|---|---|---|
| Selvol 805 | 20.5039 | 41.8407 | 17.5240 | 87.62 |
| Vitacel Oat Fiber HF600-30 | 9.9730 | 20.3511 | 8.5236 | 42.62 |
| Monomujls 90-O18 *BASF) | 2.4503 | 5.0001 | 2.0942 | 10.47 |
| Polysorbate 80 | 1.7500 | 3.5711 | 1.4957 | 7.48 |
| Dow Corning 2501 Cosmetic Wax | 1.200 | 2.4487 | 1.0256 | 5.13 |
| Kester Wax | 1.200 | 2.4487 | 1.0256 | 5.13 |
| Glycerin 99.7%, USP | 4.4784 | 9.1388 | 3.8276 | 19.14 |
| Lactic Acid, Ritalac LA | 7.4491 | 15.2008 | 6.3665 | 31.83 |
| Water, Purified | 68.000 | | 58.1173 | 290.59 |
| | | 100.0000 | 100.0000 | |
| Total Solid Weight (g) | 49.0047 | | | 209.41 |
| Total Batch Weight (g) | 117.0047 | | | 500.00 |
| % Solid | 41.88 | | | |

TABLE 5

Formulation for Skin-Contacting Layer.
Notebook #13664, Page #008

| Ingredients | Weight (g) | Solid % (in film) | % In Solution | Lab Batch (g) |
|---|---|---|---|---|
| Plasdone S-630 | 17.2800 | 41.8107 | 19.5632 | 97.8160 |
| Vitacel Oat Fiber HF600-30 | 5.000 | 12.0980 | 5.6606 | 28.3032 |
| Glycerox 767 | 1.0000 | 2.4196 | 1.1321 | 5.6606 |
| Cosmedia SP | 0.7500 | 1.8147 | 0.8491 | 4.2455 |
| Glycerin, USP 99.7% | 7.3297 | 17.7350 | 8.2982 | 41.4909 |
| Monomuls 90-O18 | 2.0561 | 4.9749 | 2.3278 | 11.6389 |
| Synovea HR, Hexylresorcinol | 0.4133 | 1.000 | 0.4679 | 2.3395 |
| Invertose HFCS 26550 (Ingredion) | 7.5000 | 18.1470 | 8.4910 | 42.4549 |
| Water, Purified | 47.0000 | | 53.2101 | 266.0505 |
| | | 100.0000 | 100.0000 | |
| Total Solid Weight (g) | 41.3291 | | | 233.9495 |
| Total Batch Weight (g) | 88.3291 | | | 500.0000 |
| % Solid | 46.79 | | | |

Again, the electrically powered patch described in Example 1 was disposed on the active substance containing self-supporting adhesive film by hand, and slight pressure was used to removably attach the two elements together.

The anti-aging prototype skin treatment device was then disposed on the face of a human subject to verify that it would adhere to the subject's skin. After several minutes, the electrically powered patch was separated from the active substance containing self-supporting adhesive film, leaving the active substance containing self-supporting adhesive film disposed on the face of the human subject.

Example 3: Formulation for Acne Treatment

A self-supporting adhesive film, made according to the process above was formed with a top layer (Table 6) and bottom layer (Table 7):

TABLE 6

Formulation for Top Layer.
Notebook #13664, Page #032

| Ingredients | Weight (g) | Solid % (in film) | % In Solution | Lab Batch (g) |
|---|---|---|---|---|
| Selvol 805 | 20.5039 | 34.5976 | 16.1113 | 80.56 |
| Vitacel Oat Fiber HF600-30 | 9.9730 | 16.8281 | 7.8364 | 39.18 |
| Monomujls 90-O18 *BASF) | 2.4503 | 4.1346 | 1.9254 | 9.63 |
| Polysorbate 80 | 1.7500 | 2.9529 | 1.3751 | 6.88 |
| Dow Corning 2501 Cosmetic Wax | 1.200 | 2.0248 | 0.9429 | 4.71 |
| Kester Wax | 1.200 | 2.0248 | 0.9429 | 4.71 |
| Glycerin 99.7%, USP | 14.7377 | 24.8679 | 11.5804 | 57.90 |
| Lactic Acid, Ritalac LA | 7.4491 | 12.5693 | 5.8533 | 29.27 |
| Water, Purified | 68.000 | | 53.4323 | 267.16 |
| | | 100.0000 | 100.0000 | |
| Total Solid Weight (g) | 59.2640 | | | 232.84 |
| Total Batch Weight (g) | 127.2640 | | | 500.00 |
| % Solid | 46.57 | | | |

TABLE 7

Formulation for Skin-Contacting Layer.
Notebook #13664, Page #008

| Ingredients | Weight (g) | Solid % (in film) | % In Solution | Lab Batch (g) |
|---|---|---|---|---|
| Plasdone S-630 | 24.0000 | 50.2837 | 30.8764 | 123.5057 |
| Polyox WSR N-10 | 5.5000 | 11.5234 | 7.0759 | 28.3034 |
| Vitacel Oat Fiber HF600-30 | 6.0000 | 12.5709 | 7.7191 | 30.8764 |
| Glycerox 767 | 1.0000 | 2.0952 | 1.2865 | 5.1461 |
| Salicylic Acid, USP, Powder | 0.9546 | 2.0000 | 1.2281 | 4.9124 |
| Aquacoat ECD, Ethylcellulose Dispersion (30%) | 10.2746 | 21.5268 | 13.2184 | 52.8737 |
| Water, Purified | 30.0000 | | 38.5955 | 154.3822 |
| | | 100.0000 | 100.0000 | |
| Total Solid Weight (g) | 47.7292 | | | 245.6178 |
| Total Batch Weight (g) | 77.7292 | | | 400.0000 |
| % Solid | 61.40 | | | |

Again, the electrically powered patch described in Example 1 was disposed on the active substance containing self-supporting adhesive film by hand, and slight pressure was used to removably attach the two elements together.

The anti-acne prototype skin treatment device was then disposed on the face of a human subject to verify that it would adhere to the subject's skin. After several minutes, the electrically powered patch was separated from the active substance containing self-supporting adhesive film, leaving the active substance containing self-supporting adhesive film disposed on the face of the human subject.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A system for delivering energy to an isolated part of a mammalian body comprising:
   (a) an electrically powered patch having a major surface and comprising a matrix of at least one flexible, biocompatible material comprising a tackifier and which is capable of conforming to the isolated body part and having associated therewith at least one active element electrically connected to a controller and a power source;
   (b) a self-supporting adhesive film having a first non-tacky surface arranged and configured for releasable attachment to the major surface of the electrically powered patch and a second tacky surface, opposite the first surface, for adhesive attachment to the isolated body part;
   wherein the releasable attachment between the self-supporting adhesive film and the major surface of the electrically powered patch has a lower strength than the adhesive attachment between the self-supporting adhesive film and the isolated body part, whereby, during use the electrically powered patch is removable from the self-supporting adhesive film while leaving the self-supporting adhesive film adhered to the isolated body part.

2. The system of claim 1 wherein the at least one active element is selected from the group consisting of a light source, a heat source, a cooling source, an electricity source, a radiofrequency source, an ultrasound source, and a motion source.

3. The system of claim 1 wherein the major surface has a surface roughness of less than about 32 Ra.

4. The system of claim 1 wherein the self-supporting adhesive film comprises at least one active substance.

5. The system of claim 1 wherein the self-supporting adhesive film is water-dispersible.

6. The system of claim 1 wherein the electrically powered patch is a master electrically powered patch and further comprising an additional electrically powered patch comprising a matrix of at least one flexible, biocompatible material which is capable of conforming to the isolated body part and having associated therewith at least one active element electrically connected to the controller and the power source of the master electrically powered patch.

7. A kit for delivering energy to an isolated part of a mammalian body comprising:
   (a) an electrically powered patch having a major surface and comprising a matrix of at least one flexible, biocompatible material comprising a tackifier and which is capable of conforming to the isolated body part and having associated therewith at least one active element electrically connected to a controller and a power source;
   (b) a supply of at least one self-supporting adhesive film, each of such self-supporting adhesive films having a first non-tacky surface arranged and configured for releasable attachment to the major surface of the electrically powered patch and a second tacky surface, opposite the first surface, for adhesive attachment to the isolated body part
   wherein the releasable attachment between the self-supporting adhesive film and the major surface of the electrically powered patch has a lower strength than the adhesive attachment of between the self-supporting adhesive film and the isolated body part, whereby, during use the electrically powered patch is removable from the self-supporting adhesive film while leaving the self-supporting adhesive film adhered to the isolated body part.

8. The system of claim 7 wherein the at least one active element is selected from the group consisting of a light source, a heat source, a cooling source, an electricity source, a radiofrequency source, an ultrasound source, and a motion source.

9. The kit of claim 7 wherein the electrically powered patch is a master electrically powered patch and further comprising an additional electrically powered patch comprising a matrix of at least one flexible, biocompatible material which is capable of conforming to the isolated body part and having associated therewith at least one active element electrically connected to the controller and the power source of the master electrically powered patch.

10. A system for delivering energy to an isolated part of a mammalian body comprising:
(a) an electrically powered patch having a major surface and comprising a matrix of at least one flexible, biocompatible material comprising a tackifier and which is capable of conforming to the isolated body part and having associated therewith at least one light-emitting active element electrically connected to a controller and a power source;
(b) a supply of at least one self-supporting adhesive film, each of such self-supporting adhesive films comprises at least one active substance, has a first non-tacky surface arranged and configured for releasable attachment to the major surface of the electrically powered patch, and has a second tacky surface, opposite the first surface, for adhesive attachment to the isolated body part;
wherein the releasable attachment between the self-supporting adhesive film and the major surface of the electrically powered patch has a lower strength than the adhesive attachment of between the self-supporting adhesive film and the isolated body part, whereby, during use the electrically powered patch is removable from the self-supporting adhesive film while leaving the self-supporting adhesive film adhered to the isolated body part.

11. The system of claim 10 wherein the major surface has a surface roughness of less than about 32 Ra.

12. The system of claim 10 wherein the self-supporting adhesive film is water-dispersible.

13. The system of claim 10 wherein the electrically powered patch is a master electrically powered patch and further comprising an additional electrically powered patch comprising a matrix of at least one flexible, biocompatible material which is capable of conforming to the isolated body part and having associated therewith at least one active element electrically connected to the controller and the power source of the master electrically powered patch.

14. A method of delivering energy to an isolated part of a mammalian body comprising the steps of:
(a) applying a first surface of a self-supporting adhesive film to a major surface of an electrically powered patch, wherein the electrically powered patch comprises a matrix of at least one flexible, biocompatible material comprising a tackifier and which is capable of conforming to the isolated body part and having associated therewith at least one active element electrically connected to a controller and a power source;
(b) adhering a second surface, opposite the first surface, of the self-supporting adhesive film to the isolated body part;
(c) energizing the active element to deliver energy through the self-supporting adhesive film and to the isolated body part;
(d) removing the electrically powered patch from the self-supporting adhesive film;
(e) applying water to the self-supporting adhesive film to remove it from the isolated body part after a period of at least about 1 minute following the removal of the electrically powered patch from the self-supporting adhesive film.

15. The method of claim 14 wherein the at least one active element is selected from the group consisting of a light source, a heat source, a cooling source, an electricity source, a radiofrequency source, an ultrasound source, and a motion source.

16. The method of claim 14 wherein step (a) occurs prior to step (b).

17. The method of claim 14 wherein step (b) occurs prior to step (a).

\* \* \* \* \*